(12) United States Patent
Aquino et al.

(10) Patent No.: US 6,432,902 B1
(45) Date of Patent: Aug. 13, 2002

(54) DETERSIVE ENZYME PARTICLES HAVING WATER-SOLUBLE CARBOXYLATE BARRIER LAYER AND COMPOSITIONS INCLUDING SAME

(75) Inventors: Melissa D. Aquino; Peter Robert Foley, both of Cincinnati, OH (US); Lynda Anne Speed, Newcastle Upon Tyne (GB); Xiaoqing Song, West Chester, OH (US); Glenn Steven Ward, Gosforth (GB); Douglas A. Dale, Pacifica, CA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/445,294

(22) PCT Filed: Jun. 2, 1998

(86) PCT No.: PCT/IB98/00847

§ 371 (c)(1),
(2), (4) Date: Dec. 3, 1999

(87) PCT Pub. No.: WO98/55577

PCT Pub. Date: Dec. 10, 1998

Related U.S. Application Data

(60) Provisional application No. 60/048,581, filed on Jun. 4, 1997.

(51) Int. Cl.[7] .............................. C11D 3/00; C11D 7/42; C12S 9/00
(52) U.S. Cl. ..................... 510/392; 510/392; 510/320; 510/374; 510/375; 435/174; 435/187; 435/188; 435/183
(58) Field of Search ................................. 510/392, 320, 510/374, 375; 435/187, 183, 188, 174

(56) References Cited

U.S. PATENT DOCUMENTS

| | | | |
|---|---|---|---|
| 4,381,247 A | 4/1983 | Nakagawa et al. | 252/95 |
| 4,526,698 A | 7/1985 | Kuroda et al. | 252/99 |
| 4,707,287 A | 11/1987 | Herdeman | 252/91 |
| 4,965,012 A | 10/1990 | Olson | 252/174.12 |
| 5,078,895 A | 1/1992 | Dany et al. | 252/94 |
| 5,093,021 A | 3/1992 | Coyne et al. | 252/91 |
| 5,254,287 A | 10/1993 | Deleeuw et al. | 252/186.27 |
| 5,332,518 A | 7/1994 | Kuroda | 252/99 |
| 5,340,496 A | 8/1994 | Sato et al. | 252/186.27 |
| 5,366,655 A | 11/1994 | Yamashita et al. | 252/186.27 |
| 5,462,804 A | 10/1995 | Kokubu et al. | 428/402.24 |
| 5,677,272 A | * 10/1997 | Ghosh et al. | 510/306 |
| 5,792,738 A | 8/1998 | Baillely et al. | 510/375 |

\* cited by examiner

Primary Examiner—Yogendra N. Gupta
Assistant Examiner—Eisa B. Elhilo
(74) Attorney, Agent, or Firm—Frank Taffy; C. Brant Cook; Kim W. Zerby

(57) ABSTRACT

A particle for detersive enzymes is disclosed by way of the present invention. The particle comprises a composite particle suitable for incorporation into a detergent composition comprising an enzyme containing core material and a water soluble carboxylate barrier layer coated on the enzyme containing core material. The preferred enzymes are protease enzymes. Automatic dishwashing compositions employing the particle are also disclosed.

25 Claims, 1 Drawing Sheet

DETERSIVE ENZYME PARTICLES HAVING WATER-SOLUBLE CARBOXYLATE BARRIER LAYER AND COMPOSITIONS INCLUDING SAME

This application claims priority from provisional application Ser. No. 60/048,581, filed Jun. 4, 1997.

TECHNICAL FIELD

The present invention relates to detersive enzyme particles having a barrier layer and compositions employing the same. More particularly, the present invention relates to a protease enzyme particle for use in automatic dishwashing compositions.

BACKGROUND OF THE INVENTION

The incorporation of detersive enzymes into automatic dishwashing detergents (ADD's) is a relatively new concept. However, it has been determined that the use of detergent protease, amylase, etc., enzymes in dishwashing compositions provides improved cleaning performance on a variety of soils.

A recognized need in ADD compositions is to have present one or more ingredients which improve the removal of tough foods and stains (e.g., tea, coffee, cocoa, etc.) from consumer articles. Strong alkalis like sodium hydroxide, bleaches such as hypochlorite, builders such as phosphates and the like can help in varying degrees. Moreover, improved ADD's make use of a source of hydrogen peroxide, optionally with a bleach activator such as TAED, as noted. In addition, enzymes such as commercial proteolytic and amylolytic enzymes can be used. The alpha-amnylase component provides at least some benefit with respect to the starchy soil removal properties of the ADD. ADD's containing amylases typically can also deliver a somewhat more moderate wash pH in use, and can remove starchy soils while avoiding delivering large weight equivalents of sodium hydroxide on a per-gram-of-product basis.

It has been also discovered that protease enzymes are particularly effective for use in promoting the cleaning properties of ADD's. However, the direct incorporation of the enzyme particles into a granular ADD composition can present problems. As noted earlier, many granular ADD formulations employ a source of hydrogen peroxide and an activator to produce an oxygen bleach system. Unfortunately, many enzyme components undergo oxidation when in contact with the components of an oxygen bleach system. Accordingly, during prolonged storage of the granular detergent ingredients, the enzyme ingredients undergo a degradation which reduces enzyme activity and overall performance of the detergent.

From the foregoing, it will be appreciated by those skilled in the art that the formulation of modern automatic dishwashing detergents is becoming increasingly complex. The need to separately manufacture, store, ship and formulate a wide variety of ingredients adds to the cost of such products. Therefore, it would be desirable to have the flexibility of formulation by the minimization of intimate contact of detergent ingredients thereby reducing some of the costs associated with the manufacture and handling of various ingredients.

Accordingly, the need remains for a granular enzyme particle which will protect the subject enzyme from oxidative degradation.

BACKGROUND ART

U.S. Pat. Nos. 4,381,247; 4,707,287; 4,965,012; 4,973,417; 5,093,021 and 5,254,287 all disclose enzyme particles for granular detergent compositions. U.S. Pat. Nos. 4,526,698; 5,078,895; 5,332,518; 5,340,496; 5,366,655; 5,462,804 and WO/95/02670 all disclose coated bleach particles.

SUMMARY OF THE INVENTION

This need is met by the present invention wherein a stabilized detersive enzyme particle for detergent compositions is provided. The enzyme particle of the present invention provides protection from oxidative degradation of the subject enzyme. The particle of the present invention employs a barrier layer on an enzyme-containing core layer. The barrier layer acts as a protective shield to the subject enzyme. If desired, additional stabilizing agents may also be added to the enzyme particle of the present invention.

Accordingly in a first embodiment of the present invention, an enzyme particle for a detersive enzyme is provided. The particle comprises a composite particle suitable for incorporation in a detergent composition comprising an enzyme-containing core material and a barrier layer coated on the enzyme-containing core material.

The preferred enzyme is a protease enzyme with the protease being derived from non-naturally-occurring carbonyl hydrolase variants having an amino acid sequence not found in nature, which is derived by replacement of a plurality of amino acid residues corresponding to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274 of a precursor carbonyl hydrolase with different amino acids, where the numbered position corresponds to naturally-occurring subtilisin from *Bacillus amyloliquefaciens*, being the most preferred and the naturally-occurring carbonyl hydrolase variants having an amino acid sequence not found in nature, which is derived by replacement of a plurality of amino acid residues corresponding to positions 76/103/104.

The enzyme core material may comprise a mixture of at least two different protease enzymes such as when at least one protease is a chymotrypsin-like protease enzyme and at least one protease is a trypsin-like protease enzyme. When employing the aforementioned mixture, the chymotrypsin-like protease enzyme is preferably a non-naturally-occurring carbonyl hydrolase variant having an amino acid sequence not found in nature, which is derived by replacement of a plurality of amino acid residues corresponding to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274 precursor carbonyl hydrolase with different amino acids, where the numbered position corresponds to naturally-occurring subtilisin from *Bacillus amyloliquefaciens* and the trypsin-like protease enzyme is a microbial alcaline proteinase.

In preferred instances, the composite particle further comprises an outer overlayer coated on the barrier layer, preferably a water-soluble polymer. Also, the enzyme containing core material may further include a bleach catalyst material or a stabilizing additive admixed in any or all of the layers, i.e. enzyme-containing core material, barrier layer and overlayer. Preferred stabilizing additives are selected from the group consisting of alkaline salts, antioxidants, chelants, radical quenchers, reducing agents and mixtures thereof with the reducing agents alkali metal sulfite, bisulfite or thiosulfate being the most preferred.

According to another embodiment of the present invention, an automatic dishwashing composition comprising, as a key component, from about 0.1% to about 20% by weight of the composition of the enzyme particle substantially as described above and from about 0.1% to about 99.9% by weight of the composition of adjunct automatic dishwashing detergent ingredients. The adjunct detergent ingredients are preferably selected from the group consisting of a source of peroxygen bleach, bleach catalysts, bleach activators, low-foaming nonionic surfactants, builders, pH-adjusting components, and mixtures thereof.

Accordingly, it is an object of the present invention to provide an enzyme particle which provides superior protection to the subject enzyme from oxidative degradation in a detergent composition. It is yet another object of the present invention to provide an enzyme particle having a barrier layer. It is still further an object of the present invention to provide an automatic dishwashing composition employing an enzyme particle having a barrier layer. These and other objects, features and advantages of the present invention will be readily apparent to one of ordinary skill in the art from the following description, drawings, and the appended claims.

All percentages, ratios and proportions herein are by weight, unless otherwise specified. Oxygen bleaches are, where noted, reported as "AvO". All documents cited herein are, in relevant part, incorporated herein by reference.

DETAILED DESCRIPTION OF THE PREFERRED EMBODIMENTS

Figure 1:
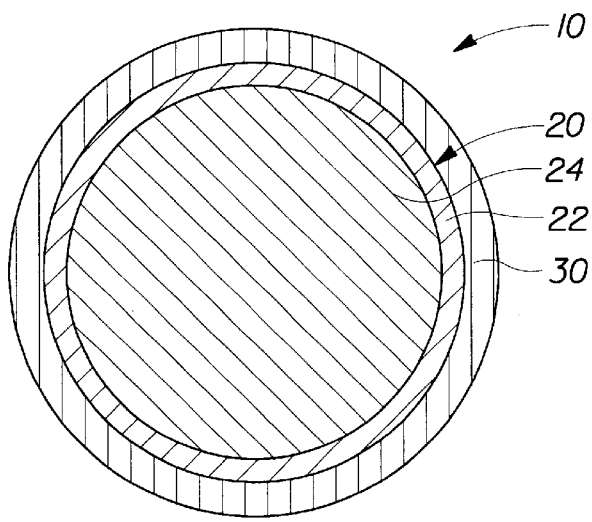
FIG. 1 is a cross-sectional view of the composite enzyme particle of the present invention.
Figure 2:
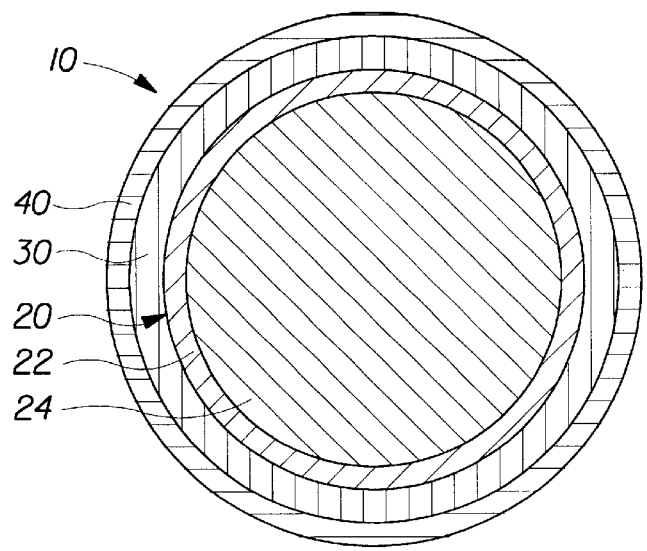
FIG. 2 is a cross-sectional view of the preferred composite particle of the present invention.
Figure 3:
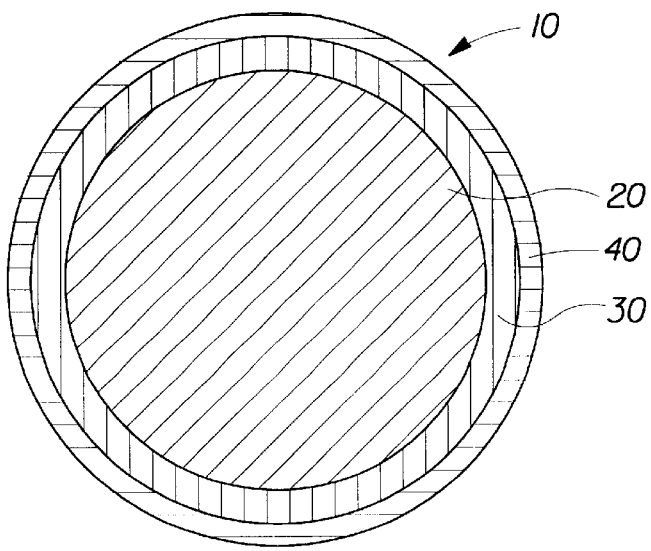
FIG. 3 is a cross-sectional view of an alternative composite enzyme particle according to the present invention.

The present invention relates to composite enzyme particles for incorporation into detergent compositions, and in particular, into automatic dishwashing compositions. Turning to FIG. 1, there is seen the composite particle 10 of the present invention. The particle 10 comprises an enzyme-containing core material 20 having a barrier layer 30 coated thereon. The enzyme core material itself comprises an enzyme layer 22 coated on carrier layer 24. Turning to FIG. 2, there is seen the preferred embodiment of the present invention wherein an overlayer 40 is coated on barrier layer 30. However, other layers may be included as is known in the art. An alternative particle according to the present invention is shown in FIG. 3. Referring to FIG. 3, there is seen an enzyme particle 10 having an enzyme containing core layer 20 wherein the enzyme is admixed with a carrier material as disclosed herein, a barrier layer 30 and an outer overlayer 40 The composite particle of the present invention, through the use of the barrier layer, provides superior protection to the enzyme from oxidative degradation from the other ingredients of a base detergent granular matrix as well as discoloration and odor generation. Accordingly, the enzyme particle of the present invention provides a significant advancement over the enzyme particles as known in the prior art.

Enzyme Containing Core Material

The enzyme containing core material, as the name implies, includes the enzyme or enzymes which the composite particle of the present invention is to deliver. The enzyme to be delivered by the present invention is a detersive enzyme. "Detersive enzyme", as used herein, means any enzyme having a cleaning, stain removing or otherwise beneficial effect in an automatic dishwashing composition. Preferred detersive enzymes are hydrolases such as proteases, amylases and lipases. Highly preferred for automatic dishwashing are amylases and/or proteases, including both current commercially available types and improved types which, though more and more bleach compatible though successive improvements, have a remaining degree of bleach deactivation susceptibility.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as dishware and the like. In practical terms for current commercial preparations, typical amounts are up to about 5 mg by weight, more typically 0.01 mg to 3 mg, of active enzyme per gram of the detergent composition. Stated otherwise, the compositions herein will typically comprise from about 0.001% to about 15%, preferably about 0.01% to about 10% by weight of a commercial enzyme preparation. Protease enzymes are usually present in such commercial preparations at levels sufficient to provide from 0.005 to 0.1 Anson units (AU) of activity per gram of composition. For certain detergents, such as in automatic dishwashing, it may be desirable to increase the active enzyme content of the commercial preparation in order to minimize the total amount of non-catalytically active materials and thereby improve spotting/filming or other end-results. Higher active levels may also be desirable in highly concentrated detergent formulations. Accordingly, the enzyme particle of the present invention is formulated to deliver the desired amount of enzyme to the wash environment.

Suitable examples of proteases within the scope of the present invention are the subtilisins which are obtained from particular strains of B. subtilis and B. licheniformis. One suitable protease is obtained from a strain of Bacillus, having maximum activity throughout the pH range of 8–12, developed and sold as ESPERASE® by Novo Industries AIS of Denmark, hereinafter "Novo". The preparation of this enzyme and analogous enzymes is described in GB 1,243,784 to Novo. Other suitable proteases include ALCALASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

In more detail, an especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +195, +197, +204, +206, +216, +260, +265, and/or +274 according to the numbering of Bacillus amyloliquefaciens subtilisin, with substitution, deletion or insertion of an amino acid residue in the following combination of residues: 76/99; 76/104; 76/99/104; 76/103/104; 76/104/107; 76/101/103/104; 76/99/101/103/104 and 76/101/104 of B. amyloliquefaciens subtilisin being preferred WO 98/55577 PCT/B98/00847 and 76/103/104 being the most preferred. Such enzymes are fully described in U.S. patent application Ser. Nos. 08/322,676 and 08/322,677, and in WO 95/10615 published Apr. 20, 1995 by Genencor International, the disclosures of which are herein incorporated by reference. Useful proteases are also described in PCT publications: WO 95130010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Amylases suitable herein, especially for, but not limited to automatic dishwashing purposes, include, for example, a-amylases described in GB 1,296,839 to Novo; RAPIDASE® International Bio-Synthetics, Inc. and TERMAMYL® Novo. FUNGAMYL® from Novo is especially useful. Engineering of enzymes for improved stability, e.g., oxidative stability, is known. See, for example J. Biological Chem., Vol. 260, No. 11, Jun. 1985, pp. 6518–6521. Certain preferred embodiments of the present compositions can make use of amylases having improved stability in detergents such as automatic dishwashing types, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/ tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Bacillus amylases, especially the Bacillus α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the B. licheniformis alpha-amylase, known as TERMAMYL®, or the homologous position variation of a similar parent amylase, such as B. amyloliquefaciens, B. subtilis, or B. stearothermophilus; (b) stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from B. licheniformis NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Other amylase enzymes include those described in WO 95/26397 and in co-pending application by Novo Nordisk PCT/DK96/00056. Specific amylase enzymes for use in the detergent compositions of the present invention include α-amylases characterized by having a specific activity at least 25% higher than the specific activity of Termamyl® at a temperature range of 25° C. to 55° C. and at a pH value in the range of 8 to 10, measured by the Phadebas® α-amnylase activity assay. (Such Phadebas® α-amylase activity assay is described at pages 9–10, WO 95/26397.) Also included herein are α-amylases which are at least 80% homologous with the amino acid sequences shown in the SEQ ID listings in the references. These enzymes are preferably incorporated into laundry detergent compositions at a level from 0.00018% to 0.060% pure enzyme by weight of the total composition, more preferably from 0.00024% to 0.048% pure enzyme by weight of the total composition.

Cellulases usable herein include both bacterial and fungal types, preferably having a pH optimum between 5 and 9.5. U.S. Pat. No. 4,435,307, Barbesgoard et al, Mar. 6, 1984, discloses suitable fungal cellulases from Humicola insolens or Humicola strain DSM 1800 or a cellulase 212-producing fungus belonging to the genus Aeromonas, and cellulase extracted from the hepatopancreas of a marine mollusk, Dolabella Auricula Solander. Suitable cellulases are also disclosed in GB-A-2.075.028; GB-A-2.095.275 and DE-OS-2.247.832. CAREZYME® and CELLUZYME® (Novo) are especially useful. See also WO 9117243 to Novo.

Suitable lipase enzymes for detergent usage include those produced by microorganisms of the Pseudomonas group, such as Pseudomonas stutzeri ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex Chromobacter viscosum, e.g. Chromobacter viscosum var. lipolyticum NRRLB 3673 from Toyo Jozo Co., Tagata, Japan; Chromobacter viscosum lipases from U.S. Biochemical Corp., U.S.A. and Disoynth Co., The Netherlands, and lipases ex Pseudomonas gladioli. LIPOLASE® enzyme derived from Humicola lanuginosa and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

In spite of the large number of publications on lipase enzymes, only the lipase derived from *Humicola lanuginosa* and produced in *Aspergillus oryzae* as host has so far found widespread application as additive for fabric washing products. It is available from Novo Nordisk under the tradename Lipolase™, as noted above. In order to optimize the stain removal performance of Lipolase, Novo Nordisk have made a number of variants. As described in WO 92105249, the D96L variant of the native *Humicola lanuginosa* lipase improves the lard stain removal efficiency by a factor 4.4 over the wild-type lipase (enzymes compared in an amount ranging from 0.075 to 2.5 mg protein per liter). Research Disclosure No. 35944 published on Mar. 10, 1994, by Novo Nordisk discloses that the lipase variant (D96L) may be added in an amount corresponding to 0.001–100- mg (5–500,000 LU/liter) lipase variant per liter of wash liquor. The present invention provides the benefit of improved whiteness maintenance on fabrics using low levels of D96L variant in detergent compositions containing the mid-chain branched surfactant surfactants in the manner disclosed herein, especially when the D96L is used at levels in the range of about 50 LU to about 8500 LU per liter of wash solution.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 A to Novo.

In addition, mixtures of the above described enzymes may also be employed. In such instances, it is desirable to employ mixtures of protease enzymes. Particularly preferred are mixtures of chymotrypsin-like protease enzymes and trypsin-like protease enzymes.

The chymotrypsin-like enzymes, according to the present invention, are those which have an activity ratio, as defined below, of greater than about 15. Particularly, preferred for this class of enzyme are those identified as "Protease D" above. Other chymotrypsin-like protease enzymes suitable for use in the present invention include those obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE® from Novo as well as the proteases known as BPN' and Carlsberg.

The trypsin-like enzymes, according to the present invention, are those which have an activity ratio, as defined below, of less than about 10, preferably less than about 8. Particularly suitable protease enzymes meeting the above requirement are microbial alcaline proteinases such as the protease enzyme obtained from *Bacillus Lentus* subtilisin including those commercially available under the tradenames SAVINASE® from Novo and PURAFECT® from Genencor International.

Other particularly preferred trypsin-like protease enzymes according to the present invention include those which are non-naturally-occurring carbonyl hydrolase variants which are derived by replacement of a plurality of amino acid residues of a precursor carbonyl hydrolase corresponding to position +210 in combination with one or more of the following residues: +33, +62, +67, +76, +100, +101, +103, +104, +107, +128, +129, +130, +132, +135, +156, +158, +164, +166, +167, +170, +209, +215, +217, +218, and +222, where the numbered position corresponds to naturally-occurring subtilisin from Bacillus amyloliquefaciens or to equivalent amino acid residues in other carbonyl hydrolases or subtilisins, such as Bacillus lentus subtilisin with different amino acids.

The preferred variant protease enzymes useful for the present invention comprise the substitution, deletion or insertion of amino acid residues in the following combinations: 210/156; 210/166; 210/76; 210/103; 210/104;–210/ 217; 210/156/166; 210/156/217; 210/166/217; 210/76/156; 210/76/166; 210/76/217; 210/761156/166; 210/76/156/217; 210/76/166/217; 210/76/103/156; 210/76/103/166; 210/76/ 103/217; 210/76/104/156; 210176/104/166; 210/76/104/ 217; 210/76/103/104/156; 210/76/103/104/166; 210/76/103/ 104/217; 210/76/103/104/156/166; 210/76/103/104/156/ 217; 210/76/103/104/166/217 and/or 210/76/103/104/156/ 1661217; 210/76/103/104/166/222; 210/6776/103/104/166/ 222; 210/67/76/103/104/166/218/222. Most preferably the variant enzymes useful for the present invention comprise the substitution, deletion or insertion of an amino acid residue in the following combination of residues: 210/156; 210/166; 210/217; 210/156/166; 210/156/217; 210/166/217; 210/76/156/166; 210/76/103/156/166 and 210/76/103/104/ 156/166 of *B. lentus* subtilisin with 210/76/103/104/156/166 being the most preferred.

The protease enzymes useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one- and three-letter codes. Such codes are identified in Dale, M. W. (1989), *Molecular Genetics of Bacteria*, John Wiley & Sons, Ltd., Appendix B.

Preferably, the substitution to be made at each of the identified amino acid residue positions include but are not limited to substitutions at position +210 including I, V, L, and A, substitutions at positions +33, +62, +76, +100, +101, +103, +104, +107, +128, +129, +130, +132, +135, +156, +158, +164, +166, +167, +170, +209, +215, +217, and +218 of D or E, substitutions at position 76 including D, H, E, G, F, K, P and N; substitutions at position 103 including Q, T, D, E, Y, K, G, R and S; and substitutions at position 104 including S, Y, I, L, M, A, W, D, T, G and V; and substitutions at position 222 including S, C, A. Trypsin-like enzymes as described above are fully disclosed in U.S. patent application Ser. No. 60/048,550, entitled "PROTEASE ENZYMES FOR TOUGH CLEANING AND COMPOSITIONS INCORPORATING SAME" to Rai et al, filed Jun. 4, 1997.

Specificity/Activity Ratio

Substrate specificity, as discussed above, is generally illustrated by the action of an enzyme on two synthetic substrates. An enzyme is placed in a solution with one of the two synthetic substrates. The capability of the enzyme in question to hydrolyze the synthetic substrate is then measured. For the purposes of the present invention, the synthetic substrates employed to measure the specificity of the enzymes of the present invention are the synthetic substrate N-Succinyl-alanyl-alanyl-prolyl-phenylalanyl-p-Nitroanilide, hereinafter suc-AAPF-pNA, and the synthetic substrate N-Benzyl-valyl-araganyl-lysyl-p-Nitroanilide, hereinafter bVGA-pNA, both of which are available from SIGMA Chemicals. Both of these synthetic substrates are well-known to one of ordinary skill in the art. A protease in the class of enzymes having trypsin-like specificity preferentially hydrolyze the synthetic substrate bVGR-pNA but hydrolyze the synthetic substrate sucAAPF-pNA to a much lesser extent. Conversely, chymotrypsin-like protease enzymes preferentially hydrolize suc-AAPF-pNA but hydrolyze the synthetic substrate bVGR-pNA to a much lesser extent.

The overall specificity of a protease enzyme can then be determined by measuring that enzyme's specificity against each of the synthetic substrates and then taking a ratio of that enzyme's activity on the two synthetic substrates. Accordingly, for the purposes of the present invention, the activity specificity ratio is determined by the formula:

[activity on suc-AAPF-pNA]/[activity on bVGR-pNA]

An enzyme having a ratio of less than about 10, more preferably less than about 8 and most preferably less than about 7 may then be considered to demonstrate trypsin-like specificity for the purposes of the present invention while an enzyme having a ratio greater than about 15, preferably greater than about 17.5 and most preferably greater than about 20 may be considered to demonstrate chymotrypsin-like Specificity for the purposes of the present invention.

For the purposes of the present invention, specificity is measured and determined against the two synthetic substrates as detailed above. The following test was employed. 5 mls of a Trisma buffer at a pH of 8.6 (prepared from a combination of 12.109 g Tris Base (0.1 M), 1.471 g $CaCl_2.2H_2O$ (0.01 M), 3.1622 g $Na_2S_2O_3$ M) pH adjusted with 1 N $H_2SO_4$) and a temperature of 25° C. is added to a standard 10 ml test tube. 0.5 ppm of the active enzyme to be tested in a IM glycine buffer is added to the test tube. Approximately, 1.25 mg of the synthetic substrate per mL of buffer solution is added to the test tube. The mixture is allowed to incubate for 15 minutes at 25° C. Upon completion of the incubation period, an enzyme inhibitor, PMSF, is added to the mixture at a level of 0.5 mg per mL of buffer solution. The absorbency or OD value of the mixture is determined on a Gilford Response UV spectrometer, Model # 1019 read at a visible light 410 nm wavelength. The absorbence then indicates the activity of the enzyme on the synthetic substrate. The greater the absorbence, the higher the level of activity against that substrate. Accordingly, absorbence is equal to enzyme activity for purposes of the present invention.

The mixed protease enzyme system of the present invention is employed in compositions at higher-end levels of from less than about 10%, more preferably less than about 5% and even more preferably less than about 2% and at lower-end levels of from greater than about 0.0001%, more preferably greater than about 0.1% and even more preferably greater than about 0.5% by weight of the composition. As for within the system itself, the ratio of chymotrypsin-like protease enzyme to trypsin-like protease enzyme ranges from about 0.5:1 to about 10:1 and more preferably from about 2:1 to about 5:1 and most preferably from about 1:1 to about 3:1. Also, preferably the protease enzyme is present in the compositions in an amount sufficient to provide a ratio of mg of active protease per 100 grams of composition to ppm theoretical Available $O_2$ ("Av$O_2$") from any peroxyacid in the wash liquor, referred to herein as the Enzyme to Bleach ratio (E/B ratio), ranging from about 1:1 to about 20:1. Several examples of various cleaning compositions wherein the protease enzymes may be employed are discussed in further detail below.

Core Manufacture

The manufacture of the core material herein comprising the enzyme can be conducted using a variety of methods, according to the desires of the formulator and the available equipment. The following illustrate various methods of manufacture, and are included for the convenience of the formulator and not by way of limitation.

The particles herein can be formulated as "marumes". Marumes and their manufacture are disclosed in U.S. Pat. No. 4,016,041 and British 1,361,387. Marumes can be prepared using an apparatus known under the trademark "Marumerizer" from Fuji Paudal, KK, and is described in U.S. Pat. No. 3,277,520 and German 1,294,351. Basically, the formation of marunes involves spheronizing extrudate noodles comprising the enzyme and a carrier. The extrudate is fed into the Marumizer® apparatus, which operates by centrifugal force on the noodles to form them into spheronized particles, referred to as "marumes".

In yet another method, the core layer herein can be manufactured in the form of "prills". Basically, in this method a slurry comprising the enzyme and a carrier melt is introduced through a spray head into a cooling chamber. The particle size of the resulting prills can be controlled by regulating the size of the spray drops of the slurry. The size of the drops will depend on the viscosity of the slurry, the spray pressure, and the like. The manufacture of prills is more fully disclosed in U.S. Pat. No. 3,749,671.

In still another method, the particles herein are made by a process comprising the following basic steps:
(i) combining the particles the dried enzyme with a carrier material while the carrier material is in a softened or molten state while agitating this combination to form a substantially uniform admixture;
(ii) rapidly cooling the resultant admixture in order to solidify it; and thereafter
(iii) further working the resulting solidified admixture, as necessary, to form the desired composite particles.

In yet another method, commercially available core materials may also be employed which may then be coated with an enzyme layer as described in U.S. Pat. No. 4,707,287, the disclosure of which is herein incorporated by reference.

Preferred methods for manufacturing the particles herein include: building-up of layers of carrier in a fluidized bed, Wurster-type coater, drum granulation, pan coaters, and like techniques for building up a granule by adding consecutive layers on top of a core material, all of which are well-known to those skilled in the art of particle manufacture. A typical process suitable for use in the manufacture of the composite particles herein is described in detail in U.S. Pat. No. 5,324,649, incorporated herein by reference.

Carrier Material

The composite particles herein may be manufactured using one or more "carrier" materials as described above which incorporate enzyme in a matrix. Since the enzyme is intended for use in an aqueous medium, the carrier material should dissolve or readily disperse in water under the intended use conditions in order to release the enzyme to perform its detersive functions. The carrier material should be inert to reaction with the enzyme components of the particle under processing conditions and after granulation. Additionally, the carrier material should preferably be substantially free of moisture present as unbound water, as noted hereinafter.

In one mode, the carrier for the soluble or dispersible composite enzyme particles herein can comprise a mixture of an inert, water-dispersible or water-soluble, typically inorganic granule material and a binder. The binder serves to provide integral particles containing the enzyme and granule material. Such particles will typically comprise: from about 50% to about 95%, by weight, of the granule material; from about 5% to about 50%, by weight, of the binder; and from about 0.01% to about 15%, by weight, of the enzyme.

Granule materials useful in such particles include inert, inorganic salts. By "inert" is meant that the salts do not deleteriously interact with the enzyme. Non-limiting examples include sodium sulfate, sodium carbonate, sodium silicate, and other ammonium and alkali metal sulfates, carbonates and silicates, and the like.

Examples of suitable organic binders include the water soluble organic homo- or co-polymeric polycarboxylic acids or their salts in which the polycarboxylic acid comprises at least two carboxyl radicals separated from each other by not more than two carbon atoms. Polymers of the latter type are disclosed in GB-A-1,596,756. Preferred examples of such compounds are the polymers which contain acrylic acid, that is to say homopolymers of acrylic acid and copolymers with any suitable other monomer units, and which have a average molecular weight of from 2,000 to 100,000. Suitable other monomer units include modified acrylic, fumaric, maleic, itaconic, aconitic, mesaconic, citraconic and methylenemalonic acid or their salts, maleic anhydride, acrylamide, alkylene, vinylmethyl ether, styrene and any mixtures thereof. Preferred are the copolymers of acrylic acid and maleic anhydride having a average molecular weight of from 20,000 to 100,000.

Preferred acrylic acid containing polymers have an average molecular weight of less than 15,000, and include those sold under the tradename Sokalan PA30, PA20, PA15, PA10 and Sokalan CP10 by BASF GmbH, and those sold under the tradename Acusol 445N by Rohm and Haas. Other suitable polymers include Acusol 450N and 410N.

Other preferred acrylic acid containing copolymers include those which contain as monomer units: a) from 90% to 10%, preferably from 80% to 20% by weight acrylic acid or its salts and b) from 10% to 90%, preferably from 20% to 80% by weight of a substituted acrylic monomer or its salts having the general formula —[$CR_2$—$CR_1$(CO—O—$R_3$)]—wherein at least one of the substituents $R_1$, $R_2$ or $R_3$, preferably $R_1$ or $R_2$ is a 1 to 4 carbon alkyl or hydroxyalkyl group, $R_1$ or $R_2$ can be a hydrogen and $R_3$ can be a hydrogen or alkali metal salt. Most preferred is a substituted acrylic monomer wherein $R_1$ is methyl, $R_2$ is hydrogen (i.e. a methacrylic acid monomer). The most preferred copolymer of this type has a average molecular weight of from 4500 to 3000 and contains 60% to 80% by weight of acrylic acid and 40% to 20% by weight of methacrylic acid. A suitable example includes Acusol 480N available from Rohm & Haas.

The polyamino compounds are useful as organic binders herein including those derived from aspartic acid such as those disclosed in EP-A-305282, EP-A-305283 and EP-A-351629.

Terpolymers containing monomer units selected from maleic acid, acrylic acid, polyaspartic acid and vinyl alcohol, particularly those having an average molecular weight of from 5,000 to 10,000, are also suitable herein.

Other organic binders suitable herein include essentially any charged and non charged cellulose derivatives such as methylcellulose, carboxymethylcellulose, hydroxypropylmethylcellulose, hydroxyethylcellulose, and ethylhydroxyethylcellulose.

Other suitable binders include the $C_{10}$–$C_{20}$ alcohol ethoxylates containing from 5–100 moles of ethylene oxide per mole of alcohol and more preferably the $C_{15}$–$C_{20}$ primary alcohol ethoxylates containing from 20–100 moles of ethylene oxide per mole of alcohol.

Other preferred binders include polyvinyl alcohol, polyvinyl acetate, the polyvinylpyrrolidones with an average molecular weight of from 12,000 to 700,000 and the polyethylene glycols (PEG) with an average molecular weight of from 600 to $5\times10^6$ preferably 1000 to 400,000 most preferably 1000 to 10,000. Copolymers of maleic anhydride with ethylene, methylvinyl ether or methacrylic acid, the maleic anhydride constituting at least 20 mole percent of the polymer are further examples of polymeric materials useful as binder agents. These polymeric materials may be used as such or in combination with solvents such as water, propylene glycol and the above mentioned $C_{10}$–$C_{20}$ alcohol ethoxylates containing from 5–100 moles of ethylene oxide per mole. Further examples of binders include the $C_{10}$–$C_{20}$ mono- and diglycerol ethers and also the $C_{10}$–$C_{20}$ fatty acids.

Other carrier materials suitable for use in the manufacture of the composite particles herein include, by way of illustration and not limitation: polyethylene glycols ("PEG") having a molecular weight typically in the range from about 1400 to about 35,000 (PEG 1400-PEG 35000) and preferably having a melting point in the range from about 38° C. to about 77° C.; fatty acids and/or fatty amides preferably having a melting point in the range from about 38° C. to about 77° C.; fatty alcohols preferably having a melting point in the range from about 38° C. to about 77° C.; the condensation products of ethylene oxide or mixed ethylene/propylene oxide and/or such condensation products of EO and/or PO with a linear or branched-chain alcohol and preferably having a melting point in the range from about 38° C. to about 77° C.; and mixtures of the foregoing. Paraffin waxes, preferably having a melting point in the range from about 38° C. to about 77° C., can also be used singly, or in combination with the foregoing carrier materials.

Also suitable as carrier materials are paraffin waxes which should melt in the range of from about 38° C. (100° F.) to about 43° C. (110° F.), $C_{16}$–$C_{20}$ fatty acids and ethoxylated $C_{16}$–$C_{20}$ alcohols. Mixtures of suitable carrier materials are also envisaged.

Various other materials may be used in the carrier, including finely divided cellulosic fibers (see U.S. Pat. No. 4,106,991) sugars, starches, and the like, according to the desires of the formulator. If used, such other materials will typically comprise from about 2% to about 50%, by weight, of the composite particles herein.

Barrier Layer

The barrier layer of the composite particle of the present invention comprises a water soluble carboxylate compound. While other ingredients may be included in the barrier layer, the barrier layer is predominately water-soluble carboxylate. Typically, the barrier layer includes at least about 50% water-soluble carboxylate and more preferably comprises at least 75% water-soluble carboxylate. For the purposes of the present invention, the phrase "water soluble carboxylate compound" includes carboxylates, dicarboxylates and polycarboxylate anions. Preferably, the water soluble carboxylate is a salt of a metal or nitrogen-based cation. Preferred metals include the alkali metals such as sodium. Preferred nitrogen-based cations include ammonium compounds. Preferred carboxylate compounds include citrates, succinates and maleates with citrates being the more preferred and sodium citrate hydrate the most preferred. Of course, mixtures of carboxylates may also be employed. While not wishing to be bound by theory, it is believed that the barrier compound, and in particular, the sodium citrate forms a tight crystal structure around the particle which then acts as a barrier to oxidative degradation. Accordingly, via the use of the barrier layer, a superior enzyme particle is provided. The barrier layer is employed at levels of from about 1% to about 50% by weight of the particle, preferably from about 5% to about 40% and most preferably from about 10% to about 30%.

Outer Overlayer

An outer overlayer is optionally, but preferably, applied over the barrier layer. The overlayer may provide a number of additional benefits to the enzyme particle of the present invention including, but not limited to, an additional level of protection to the enzyme containing core, reduced dusting, enhanced solubility, etc. The overlayer need not provide for stability of the enzyme in the absence of the barrier layer, but it should be sufficiently non-reactive in the presence of the barrier layer to active in conjunction with the barrier layer in reducing oxidative attack. The overlayer is typically present at levels of from about 0.1% to about 60%, and more preferably from about 1% to about 30%.

Appropriate materials include water-soluble polymers, fatty acids, waxes, surfactants/dispersants and alkaline materials, all as hereinbefore described as "carrier" materials. Examples of water-soluble polymers include, but is not limited to, polyacrylic acids, polyethylene glycols, polyvinyl alcohols, polyvinylpyrrolidone, starches, and most preferred, celluloses such as hydroxy propyl methyl cellulose. Suitable surfactants include nonionic surfactants and wetting agents such as Neodol® from Shell Oil Co. and Triton® from Rohm and Haas. Suitable examples of alkaline materials include silicates, carbonates and bicarbonates, particularly alkali metals such as sodium silicate and sodium carbonate. In addition, the outer layer may comprise various "free-flow" agents such as clays and zeolites.

Lastly, the outer layer may include various additives, including, but not limited to, whiteners, pigments, fillers such as $CaCO_3$ and talc, plasticizers such as PEG and PVP or other coloring agents, such as $TiO_2$.

Stabilizing Additive

The composite particles of the present invention may include a stabilizing additive to enhance the stability of the enzyme, i.e reduce oxidation, minimize odor, etc. The stabilizing additive may be added to each or all layers of the composite particle including the enzyme-containing core, barrier layer and outer overlayer. The stabilizing additive according to the present invention may be present in the particle at levels of from about 0.1% to about 60% by weight of the particle, and more preferably from about 0.1% to about 25% by weight of the particle, and most preferably from about 0.5% to about 10% by weight of the particle.

The term "stabilizer," as used herein, includes antioxidants, chelants, radical quenchers, alkaline ingredients and reductive agents. These assure good odor and enzyme stability under long term storage conditions for the compositions.

Examples of antioxidants that can be added to the compositions of this invention include a mixture of ascorbic acid, ascorbic palmitate, propyl gallate, available from Eastman Chemical Products, Inc., under the trade names Tenox® PG and Tenox S-1; butylated hydroxytoluene, available from UOP Process Division under the trade name Sustane® BHT; tertiary butylhydroquinone, Eastman Chemical Products, Inc., as Tenox TBHQ; natural tocopherols, Eastman Chemical Products, Inc., as Tenox GT-1/GT-2; and butylated hydroxyanisole, Eastman Chemical Products, Inc., as BHA. Of course, any of the ingredients in these mixtures, such as ascorbic acid, ascorbic palmitate, BHT, BHQ and BHA, may be employed individually as well Examples of reductive agents include sodium borohydride, hypophosphorous acid, sulfites, thiosulfates and bisulfites particularly the alkali metals such as sodium and mixtures thereof.

Examples of suitable radical quenchers for use in the present invention include the Tinuvin series available from Ciba-Geigy.

Alkaline materials suitable for use in the present invention include silicates, carbonates and bicarbonates, particularly the alkali metals such as sodium. Chelating agents may be selected from the group consisting of amino carboxylates, amino phosphonates, polyfunctionally-substituted aromatic chelating agents and mixtures therein, all as hereinafter defined.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the particles of the invention when at least low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A biodegradable chelator available for use herein is ethylenediamine disuccinate ("EDDS"), especially the [S,S] isomer as described in U.S. Pat. No. 4,704,233, Nov. 3, 1987, to Hartman and Perkins.

Particle Water Content

The final composite particles should have a low free water content to favor in-product stability and minimize the stickiness of the composite particles. The composite particles should preferably have a free water content of less than about 10%, preferably less than about 6%, more preferably less than about 3%, and most preferably less than 1%. Excess free water can be removed by standard drying processes.

Detergent Compositions

The composite particles herein are useful components of detergent compositions, particularly those designed for use in dishwashing operations, but including laundry compositions as well. Such detergent compositions may additionally contain any known detergent components, particularly those selected from pH-adjusting and detergency builder components, other bleaches, bleach activators, silicates, dispersant polymers, low-foaming nonionic surfactants, anionic co-surfactants, enzyme stabilizers, suds suppressors, corrosion inhibitors, fillers, hydrotropes and perfumes.

A preferred granular or powdered detergent composition comprises by weight:

(a) from about 0.1% to about 10% of the enzyme composite particles as hereinbefore described;

(b) a bleach component comprising from about 0.01% to about 8% (as available oxygen "AvO") of a peroxygen bleach;

(c) from about 0.1% to about 90% of a pH adjusting component consisting of water-soluble salt, builder or salt/builder mixture selected from STPP, sodium carbonate, sodium sesquicarbonate, sodium citrate, citric acid, sodium bicarbonate, sodium hydroxide, and mixtures thereof;

(d) from about 3% to about 20% silicate (as $SiO_2$);

(e) from 0% to about 10% of a low-foaming nonionic surfactant, especially other than an amine oxide;

(f) from 0% to about 10% of a suds suppressor;

(g) from 0% to about 25% of a dispersant polymer.

Such compositions are typically formulated to provide an in-use wash solution pH from about 9.5 to about 11.5.

Enzyme Stabilizing System

Enzyme-containing compositions, herein may comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

One stabilizing approach is the use of water-soluble sources of calcium and/or magnesium ions in the finished compositions which provide such ions to the enzymes. Calcium ions are generally more effective than magnesium ions and are preferred herein if only one type of cation is being used. Typical detergent compositions, especially liquids, will comprise from about 1 to about 30, preferably from about 2 to about 20, more preferably from about 8 to about 12 millimoles of calcium ion per liter of finished detergent composition, though variation is possible depending on factors including the multiplicity, type and levels of enzymes incorporated. Preferably water-soluble calcium or magnesium salts are employed, including for example calcium chloride, calcium hydroxide, calcium formate, calcium malate, calcium maleate, calcium hydroxide and calcium acetate; more generally, calcium sulfate or magnesium salts corresponding to the exemplified calcium salts may be used. Further increased levels of Calcium and/or Magnesium may of course be useful, for example for promoting the grease-cutting action of certain types of surfactant.

Another stabilizing approach is by use of borate species. See Severson, U.S. Pat. No. 4,537,706. Borate stabilizers, when used, may be at levels of up to 10% or more of the composition though more typically, levels of up to about 3% by weight of boric acid or other borate compounds such as borax or orthoborate are suitable for liquid detergent use. Substituted boric acids such as phenylboronic acid, butaneboronic acid, p-bromophenylboronic acid or the like can be used in place of boric acid and reduced levels of total boron in detergent compositions may be possible though the use of such substituted boron derivatives.

Stabilizing systems of example automatic dishwashing compositions, may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during dishwashing, can be relatively large; accordingly, enzyme stability to chlorine in-use is sometimes problematic. Since perborate or percarbonate, which have the ability to react with chlorine bleach, may present in certain of the instant compositions in amounts accounted for separately from the stabilizing system, the use of additional stabilizers against chlorine, may, most generally, not be essential, though improved results may be obtainable from their use. Suitable chlorine scavenger anions are widely known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used. Likewise, special enzyme inhibition systems can be incorporated such that different enzymes have maximum compatibility. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired. In general, since the chlorine scavenger function can be performed by ingredients separately listed under better recognized functions, (e.g., hydrogen peroxide sources), there is no absolute requirement to add a separate chlorine scavenger unless a compound performing that function to the desired extent is absent from an enzyme-containing embodiment of the invention; even then, the scavenger is added only for optimum results. Moreover, the formulator will exercise a chemist's normal skill in avoiding the use of any enzyme scavenger or stabilizer which is majorly incompatible, as formulated, with other reactive ingredients, if used. In relation to the use of ammonium salts, such salts can be simply admixed with the detergent composition but are prone to adsorb water and/or liberate ammonia during storage. Accordingly, such materials, if present, are desirably protected in a particle such as that described in US 4,652,392, Baginski et al.

Detergent Salts

The present invention may include a suitable builder or detergency salt. The level of detergent salt/builder can vary widely depending upon the end use of the composition and its desired physical form. When present, the compositions will typically comprise at least about 1% builder and more typically from about 10% to about 80%, even more typically from about 15% to about 50% by weight, of the builder. Lower or higher levels, however, are not meant to be excluded.

Inorganic or P-containing detergent salts include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate salts are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate salts as builders are the alkaline earth and alkali metal carbonates as disclosed in German Patent Application No. 2,321,001 published on Nov. 15, 1973.

Aluminosilicate builders may also be added to the present invention as a detergent salt. Aluminosilicate builders are of great importance in most currently marketed heavy duty granular detergent compositions. Aluminosilicate builders include those having the empirical formula:

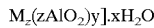

$M_z(zAlO_2)y] \cdot xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

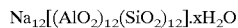

$Na_{12}[(AlO_2)_{12}(SiO_2)_{12}] \cdot xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance. Oxydisuccinates are also especially useful in such compositions and combinations.

Also suitable in the detergent compositions of the present invention are the 3,3-dicarboxy4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

Surfactants

Detersive surfactants included in the fully-formulated detergent compositions afforded by the present invention comprises at least 0.01%, preferably from about 0.5% to about 50%, by weight of detergent composition depending upon the particular surfactants used and the desired effects. In a highly preferred embodiment, the detersive surfactant comprises from about 0.5% to about 20% by weight of the composition.

The detersive surfactant can be nonionic, anionic, ampholytic, zwitterionic, or cationic. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. Other conventional useful surfactants are listed in standard texts.

Particularly preferred surfactants in the preferred automatic dishwashing compositions (ADD) of the present invention are low foaming nonionic surfactants (LFNI). LFNI may be present in amounts from 0.01% to about 10% by weight, preferably from about 0.1% to about 10%, and most preferably from about 0.25% to about 4%. LFNIs are most typically used in ADDs on account of the improved water-sheeting action (especially from glass) which they confer to the ADD product. They also encompass non-silicone, nonphosphate polymeric materials further illustrated hereinafter which are known to defoam food soils encountered in automatic dishwashing.

Preferred LFNIs include nonionic alkoxylated surfactants, especially ethoxylates derived from primary alcohols, and blends thereof with more sophisticated surfactants, such as the polyoxypropylene/polyoxyethylene/polyoxypropylene (PO/EOIPO) reverse block polymers. The PO/EO/PO polymer-type surfactants are well-known to have foam suppressing or defoaming action, especially in relation to common food soil ingredients such as egg.

The invention encompasses preferred embodiments wherein LFNI is present, and wherein this component is solid at about 95° F. (35° C.), more preferably solid at about 77° F. (250° C.). For ease of manufacture, a preferred LFNI has a melting point between about 77° F. (25° C.) and about 140° F. (60° C.), more preferably between about 80° F. (26.6° C.) and 110° F. (43.3° C.).

In a preferred embodiment, the LFNI is an ethoxylated surfactant derived from the reaction of a monohydroxy alcohol or alkylphenol containing from about 8 to about 20 carbon atoms, with from about 6 to about 15 moles of ethylene oxide per mole of alcohol or alkyl phenol on an average basis.

A particularly preferred LFNI is derived from a straight chain fatty alcohol containing from about 16 to about 20 carbon atoms ($C_{16}$–$C_{20}$ alcohol), preferably a $C_{18}$ alcohol, condensed with an average of from about 6 to about 15 moles, preferably from about 7 to about 12 moles, and most preferably from about 7 to about 9 moles of ethylene oxide per mole of alcohol. Preferably the ethoxylated nonionic surfactant so derived has a narrow ethoxylate distribution relative to the average.

The LFNI can optionally contain propylene oxide in an amount up to about 15% by weight. Other preferred LFNI surfactants can be prepared by the processes described in U.S. Pat. No. 4,223,163, issued Sep. 16, 1980, Builloty, incorporated herein by reference.

Highly preferred ADDs herein wherein the LFNI is present make use of ethoxylated monohydroxy alcohol or alkyl phenol and additionally comprise a polyoxyethylene, polyoxypropylene block polymeric compound; the ethoxylated monohydroxy alcohol or alkyl phenol fraction of the LFNI comprising from about 20% to about 100%, preferably from about 30% to about 70%, of the total LFNI.

Suitable block polyoxyethylene-polyoxypropylene polymeric compounds that meet the requirements described hereinbefore include those based on ethylene glycol, propylene glycol, glycerol, trimethylolpropane and ethylenediamine as initiator reactive hydrogen compound. Polymeric compounds made from a sequential ethoxylation and propoxylation of initiator compounds with a single reactive hydrogen atom, such as $C_{12-18}$ aliphatic alcohols, do not generally provide satisfactory suds control in the instant ADDs. Certain of the block polymer surfactant compounds designated PLURONIC® and TETRONIC® by the BASF-Wyandotte Corp., Wyandotte, Mich. are suitable in ADD compositions of the invention.

A particularly preferred LFNI contains from about 40% to about 70% of a polyoxypropylene/polyoxyethylene/polyoxypropylene block polymer blend comprising about 75%, by weight of the blend, of a reverse block co-polymer of polyoxyethylene and polyoxypropylene containing 17 moles of ethylene oxide and 44 moles of propylene oxide; and about 25%, by weight of the blend, of a block co-polymer of polyoxyethylene and polyoxypropylene initiated with trimethylolpropane and containing 99 moles of propylene oxide and 24 moles of ethylene oxide per mole of trimethylolpropane.

Suitable for use as LFNI in the ADD compositions are those LFNI having relatively low cloud points and high hydrophilic-lipophilic balance (HLB). Cloud points of 1% solutions in water are typically below about 32° C. and preferably lower, e.g., 0° C., for optimum control of sudsing throughout a full range of water temperatures.

LFNIs which may also be used include those POLY-TERGENT® SLF-18 nonionic surfactants from Olin Corp., and any biodegradable LFNI having the melting point properties discussed hereinabove.

These and other nonionic surfactants are well known in the art, being described in more detail in Kirk Othmer's Encyclopedia of Chemical Technology, 3rd Ed., Vol. 22, pp. 360–379, "Surfactants and Detersive Systems", incorporated by reference herein.

Preferred are ADD compositions comprising mixed surfactants wherein the sudsing (absent any silicone suds controlling agent) is less than 2 inches, preferably less than 1 inch, as determined by the disclosure below.

The equipment useful for these measurements are: a Whirlpool Dishwasher (model 900) equipped with clear plexiglass door, IBM computer data collection with Labview and Excel Software, proximity sensor (Newark Corp. - model 95F5203) using SCXI interface, and a plastic ruler.

The data is collected as follows. The proximity sensor is affixed to the bottom dishwasher rack on a metal bracket. The sensor faces downward toward the rotating dishwasher arm on the bottom of the machine (distance approximately 2 cm. from the rotating arm). Each pass of the rotating arm is measured by the proximity sensor and recorded. The pulses recorded by the computer are converted to rotations per minute (RPM) of the bottom arm by counting pulses over a 30 second interval. The rate of the arm rotation is directly proportional to the amount of suds in the machine and in the dishwasher pump (i.e., the more suds produced, the slower the arm rotation).

The plastic ruler is clipped to the bottom rack of the dishwasher and extends to the floor of the machine. At the end of the wash cycle, the height of the suds is measured using the plastic ruler (viewed through the clear door) and recorded as suds height.

The following procedure is followed for evaluating ADD compositions for suds production as well as for evaluating nonionic surfactants for utility. (For separate evaluation of nonionic surfactant, a base ADD formula, such as Cascade powder, is used along with the nonionic surfactants which are added separately in glass vials to the dishwashing machine.)

First, the machine is filled with water (adjust water for appropriate temperature and hardness) and proceed through a rinse cycle. The RPM is monitored throughout the cycle (approximately 2 min.) without any ADD product (or surfactants) being added (a quality control check to ensure the machine is functioning properly). As the machine begins to fill for the wash cycle, the water is again adjusted for temperature and hardness, and then the ADD product is added to the bottom of the machine (in the case of separately evaluated surfactants, the ADD base formula is first added to the bottom of the machine then the surfactants are added by placing the surfactant-containing glass vials inverted on the top rack of the machine). The RPM is then monitored throughout the wash cycle. At the end of the wash cycle, the suds height is recorded using the plastic ruler. The machine is again filled with water (adjust water for appropriate temperature and hardness) and runs through another rinse cycle. The RPM is monitored throughout this cycle.

An average RPM is calculated for the 1st rinse, main wash, and final rinse. The %RPM efficiency is then calculated by dividing the average RPM for the test surfactants into the average RPM for the control system (base ADD formulation without the nonionic surfactant). The RPM efficiency and suds height measurements are used to dimension the overall suds profile of the surfactant.

Bleaching Agents

Hydrogen peroxide sources are described in detail in the herein incorporated Kirk Othmer's Encyclopedia of Chemical Technology, 4th Ed (1992, John Wiley & Sons), Vol. 4, pp. 271–300 "Bleaching Agents (Survey)", and include the various forms of sodium perborate and sodium percarbonate, including various coated and modified forms. An "effective amount" of a source of hydrogen peroxide is any amount capable of measurably improving stain removal (especially of tea stains) from soiled dishware compared to a hydrogen peroxide source-free composition when the soiled dishware is washed by the consumer in a domestic automatic dishwasher in the presence of alkali.

More generally a source of hydrogen peroxide herein is any convenient compound or mixture which under consumer use conditions provides an effective amount of hydrogen peroxide. Levels may vary widely and are usually in the range from about 0.1% to about 70%, more typically from about 0.5% to about 30%, by weight of the ADD compositions herein.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

While not preferred for ADD compositions of the present invention which comprise detersive enzymes, the present invention compositions may also comprise as the bleaching agent a chlorine-type bleaching material. Such agents are well known in the art, and include for example sodium dichloroisocyanurate ("NaDCC").

While effective ADD compositions herein may comprise only the nonionic surfactant and builder, fully-formulated ADD compositions typically will also comprise other automatic dishwashing detergent adjunct materials to improve or modify performance. These materials are selected as appropriate for the properties required of an automatic dishwashing composition. For example, low spotting and filming is desired—preferred compositions have spotting and filming grades of 3 or less, preferably less than 2, and most preferably less than 1, as measured by the standard test of The American Society for Testing and Materials ("ASTM") D3556–85 (Reapproved 1989) "Standard Test Method for Deposition on Glassware During Mechanical Dishwashing".

(a) Bleach Activators

The peroxygen bleach component in the composition may be formulated with an activator (peracid precursor). The activator is present at levels of from about 0.01% to about 15%, preferably from about 0.5% to about 10%, more preferably from about 1% to about 8%, by weight of the composition. Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group.

Preferred bleach activators are those described in U.S. Pat. No. 5,130,045, Mitchell et al, and 4,412,934, Chung et al, and copending patent applications U.S. Ser. Nos. 08/064,624, 08/064,623, 08/064,621, 08/064,562, 08/064,564, 08/082,270 and copending application to M. Burns, A. D. Willey, R. T. Hartshom, C. K. Ghosh, entitled "Bleaching Compounds Comprising Peroxyacid Activators Used With Enzymes" and having U.S. Ser. No. 08/133,691 (P&G Case 4890R), all of which are incorporated herein by reference.

The mole ratio of peroxygen bleaching compound (as AvO) to bleach activator in the present invention generally ranges from at least 1:1, preferably from about 20:1 to about 1:1, more preferably from about 10:1 to about 3:1.

Quaternary substituted bleach activators may also be included. The present detergent compositions preferably comprise a quaternary substituted bleach activator (QSBA) or a quaternary substituted peracid (QSP); more preferably, the former. Preferred QSBA structures are further described in copending U.S. Ser. Nos. 08/298,903, 08/298,650, 08/298,906 and 08/298,904 filed Aug. 31, 1994, incorporated herein by reference.

(b) Organic Peroxides. especially Diacyl Peroxides

These are extensively illustrated in Kirk Othmer, Encyclopedia of Chemical Technology, Vol. 17, John Wiley and Sons, 1982 at pages 27–90 and especially at pages 63–72, all incorporated herein by reference. If a diacyl peroxide is used, it will preferably be one which exerts minimal adverse impact on spotting/filming.

(c) Metal-containing Bleach Catalysts

The present invention compositions and methods utilize metal-containing bleach catalysts that are effective for use in ADD compositions. Preferred are manganese and cobalt-containing bleach catalysts.

One type of metal-containing bleach catalyst is a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

Other types of bleach catalysts include the manganese-based complexes disclosed in U.S. Pat. No. 5,246,621 and U.S. Pat. No. 5,244,594. Preferred examples of theses catalysts include $Mn^{IV}_2(u\text{-}O)_3(1,4,7\text{-trimethyl-}1,4,7\text{-triazacyclononane})_2\text{-}(PF_6)_2$ ("MnTACN"), $Mn^{III}_2(u\text{-}O)_1(u\text{-}OAc)_2(1,4,7\text{-trimethyl-}1,4,7\text{-triazacyclononane})_2\text{-}(ClO_4)_2$, $Mn^{IV}_4(u\text{-}O)_6(1,4,7\text{-triazacyclononane})_4\text{-}(ClO_4)_2$, $Mn^{III}Mn_{IV4}(u\text{-}OAc)_2(1,4,7\text{-trimethyl-}1,4,7\text{-triazacyclononane})_2\text{-}(ClO_4)_3$, and mixtures thereof. See also European patent application publication no. 549,272. Other ligands suitable for use herein include 1,5,9-trimethyl-1,5,9-triazacyclododecane, 2-methyl-1,4,7-triazacyclononane, 2-methyl-1,4,7-triazacyclononane, and mixtures thereof.

The bleach catalysts useful in automatic dishwashing compositions and concentrated powder detergent compositions may also be selected as appropriate for the present invention. For examples of suitable bleach catalysts see U.S. Pat. No. 4,246,612 and U.S. Pat. No. 5,227,084.

Other bleach catalysts are described, for example, in European patent application, publication no. 408,131 (cobalt complex catalysts), European patent applications, publication nos. 384,503, and 306,089 (metallo-porphyrin catalysts), U.S. Pat. No. 4,728,455 (manganese/multidentate ligand catalyst), U.S. Pat. No. 4,711,748 and European patent application, publication no. 224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), German Patent specification 2,054,019 (cobalt chelant catalyst) Canadian 866,191 (transition metal-containing salts), U.S. Pat. No. 4,430,243 (chelants with manganese cations and non-catalytic metal cations), and U.S. Pat. No. 4,728,455 (manganese gluconate catalysts).

Preferred are cobalt catalysts which have the formula:

$$[Co(NH_3)_n(M')_m]Y_y$$

wherein n is an integer from 3 to 5 (preferably 4 or 5; most preferably 5); M' is a labile coordinating moiety, preferably selected from the group consisting of chlorine, bromine, hydroxide, water, and (when m is greater than 1) combinations thereof; m is an integer from 1 to 3 (preferably 1 or 2; most preferably 1) m+n=6; and Y is an appropriately selected counteranion present in a number y, which is an integer from 1 to 3 (preferably 2 to 3; most preferably 2 when Y is a −1 charged anion), to obtain a charge-balanced salt.

The preferred cobalt catalyst of this type useful herein are cobalt pentaamine chloride salts having the formula [Co(NH_3)_5Cl]Y_y, and especially $[Co(NH_3)_5Cl]Cl_2$.

More preferred are the present invention compositions which utilize cobalt (III) bleach catalysts having the formula:

$$[Co(NH_3)_n(M)_m(B)_b]T_y$$

wherein cobalt is in the +3 oxidation state; n is 4 or 5 (preferably 5); M is one or more ligands coordinated to the cobalt by one site; m is 0, 1 or 2 (preferably 1); B is a ligand coordinated to the cobalt by two sites; b is 0 or 1 (preferably 0), and when b=0, then m+n=6, and when b=1, then m=0 and n=4; and T is one or more appropriately selected counteranions present in a number y, where y is an integer to obtain a charge-balanced salt (preferably y is 1 to 3; most preferably 2 when T is a −1 charged anion); and wherein further said catalyst has a base hydrolysis rate constant of less than 0.23 $M^{-1}_{s-1}$(25° C.).

Preferred T are selected from the group consisting of chloride, iodide, $I_3-$, formate, nitrate, nitrite, sulfate, sulfite, citrate, acetate, carbonate, bromide, $PF_6-$, $BF_4-$, $B(Ph)_4-$, phosphate, phosphite, silicate, tosylate, methanesulfonate, and combinations thereof. Optionally, T can be protonated if more than one anionic group exists in T, e.g., $HPO_4^{2-}$, $HCO_3-$, $H_2PO_4-$, etc. Further, T may be selected from the group consisting of non-traditional inorganic anions such as anionic surfactants (e.g., linear alkylbenzene sulfonates (LAS), alkyl sulfates (AS), alkylethoxysulfonates (AES), etc.) and/or anionic polymers (e.g., polyacrylates, polymethacrylates, etc.).

The M moieties include, but are not limited to, for example, $F^-$, $SO_4^{-2}$, $NCS^-$, $SCN^-$, $S_2O_3^{-2}$, $NH_3$, $PO_4^{3-}$, and carboxylates (which preferably are mono-carboxylates, but more than one carboxylate may be present in the moiety as long as the binding to the cobalt is by only one carboxylate per moiety, in which case the other carboxylate in the M moiety may be protonated or in its salt form). Optionally, M can be protonated if more than one anionic group exists in M (e.g., $HPO_4^{2-}$, $HCO_3-$, $H_2PO_4-$, $HOC(O)CH_2C(O)O-$, etc.) Preferred M moieties are substituted and unsubstituted $C_1$–$C_{30}$ carboxylic acids having the formulas:

$$RC(O)O—$$

wherein R is preferably selected from the group consisting of hydrogen and $C_1$–$C_{30}$ (preferably $C_1$–$C_{18}$) unsubstituted and substituted alkyl, $C_6$–$C_{30}$ (preferably $C_6$–$C_{18}$) unsubstituted and substituted aryl, and $C_3$–$C_{30}$ (preferably $C_5$–$C_{18}$) unsubstituted and substituted heteroaryl, wherein substituents are selected from the group consisting of $—NR'_3$, $—NR'_4+$, $—C(O)OR'$, $—OR'$, $—C(O)NR'_2$, wherein R' is selected from the group consisting of hydrogen and $C_1$–$C_6$ moieties. Such substituted R therefore include the moieties —$(CH_2)_n OH$ and —$(CH_2)_n NR'_4+$, wherein n is an integer from 1 to about 16, preferably from about 2 to about 10, and most preferably from about 2 to about 5.

Most preferred M are carboxylic acids having the formula above wherein R is selected from the group consisting of hydrogen, methyl, ethyl, propyl, straight or branched $C_4$–$C_{12}$ alkyl, and benzyl. Most preferred R is methyl. Preferred carboxylic acid M moieties include formic, benzoic, octanoic, nonanoic, decanoic, dodecanoic, malonic, maleic, succinic, adipic, phthalic, 2-ethylhexanoic, naphthenoic, oleic, palmitic, triflate, tartrate, stearic, butyric, citric, acrylic, aspartic, fumaric, lauric, linoleic, lactic, malic, and especially acetic acid.

The B moieties include carbonate, di- and higher carboxylates (e.g., oxalate, malonate, malic, succinate, maleate), picolinic acid, and alpha and beta amino acids (e.g., glycine, alanine, beta-alanine, phenylalanine).

Cobalt bleach catalysts useful herein are known, being described for example along with their base hydrolysis rates, in M. L. Tobe, "Base Hydrolysis of Transition-Metal Complexes", *Adv. Inorg. Bioorg. Mech.*, (1983), 2, pages 1–94. For example, Table 1 at page 17, provides the base hydrolysis rates (designated therein as $k_{OH}$) for cobalt pentaamine catalysts complexed with oxalate ($k_{OH}$=2.5×10$^{-4}$M$_s^{-1}$(25° C.)), NCS—($k_{OH}$=5.0 ×10$^{-4}$M$_s^{-1}$ (25° C.)), formate ($k_{OH}$=5.8×10$^{-4}$M$_s^{-1}$(25° C.)), and acetate ($k_{OH}$=9.6×10$^{-4}$M$_s^{-1}$(25° C.)). The most preferred cobalt catalyst useful herein are cobalt pentaamine acetate salts having the formula [Co(NH$_3$)$_5$OAc] T$_y$, wherein OAc represents an acetate moiety, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF4)$_4$)$_2$; and [Co(NH$_3$)$_5$OAc](NO$_3$)$_2$.

These cobalt catalysts are readily prepared by known procedures, such as taught for example in the Tobe article hereinbefore and the references cited therein, in U.S. Pat. No. 4,810,410, to Diakun et al, issued Mar. 7,1989, *J. Chem. Ed.* (1989), 66 (12), 1043–45; The Synthesis and Characterization of Inorganic Compounds, W. L. Jolly (Prentice-Hall; 1970), pp. 461–3; *Inorg. Chem.*, 18 1497–1502 (1979); *Inorg. Chem.*, 21 2881–2885 (1982); *Inorg. Chem.*, 18, 2023–2025 (1979); Inorg. Synthesis, 173–176 (1960); and *Journal of Physical Chemistry*, 56, 22–25 (1952).

These catalysts may be coprocessed with adjunct materials so as to reduce the color impact if desired for the aesthetics of the product, or to be included in enzyme-containing particles as exemplified hereinafter, or the compositions may be manufactured to contain catalyst "speckles".

As a practical matter, and not by way of limitation, the cleaning compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic dishwashing process, typical automatic dishwashing compositions herein will comprise from about 0.0005% to about 0.2%, more preferably from about 0.004% to about 0.08%, of bleach catalyst by weight of the cleaning compositions.

PH and Buffering Variation

Many detergent compositions herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH jump systems, dual compartment containers, etc., and are well known to those skilled in the art.

The preferred ADD compositions herein comprise a pH-adjusting component selected from water-soluble alkaline inorganic salts and water-soluble organic or inorganic builders. The pH-adjusting components are selected so that when the ADD is dissolved in water at a concentration of 1,000–10,000 ppm, the pH remains in the range of above about 8, preferably from about 9.5 to about 11.5. The preferred nonphosphate pH-adjusting component of the invention is selected from the group consisting of:

(i) sodium carbonate or sesquicarbonate;
(ii) sodium silicate, preferably hydrous sodium silicate having $SiO_2$:$Na_2O$ ratio of from about 1:1 to about 2:1, and mixtures thereof with limited quantities of sodium metasilicate;
(iii) sodium citrate;
(iv) citric acid;
(v) sodium bicarbonate;
(vi) sodium borate, preferably borax;
(vii) sodium hydroxide; and
(viii) mixtures of (i)-(vii).

Preferred embodiments contain low levels of silicate (i.e. from about 3% to about 10% $SiO_2$).

Illustrative of highly preferred pH-adjusting component systems are binary mixtures of granular sodium citrate with anhydrous sodium carbonate, and three-component mixtures of granular sodium citrate trihydrate, citric acid monohydrate and anhydrous sodium carbonate.

The amount of the pH adjusting component in the instant ADD compositions is preferably from about 1% to about 50%, by weight of the composition. In a preferred embodiment, the pH-adjusting component is present in the ADD composition in an amount from about 5% to about 40%, preferably from about 10% to about 30%, by weight.

For compositions herein having a pH between about 9.5 and about 11 of the initial wash solution, particularly preferred ADD embodiments comprise, by weight of ADD, from about 5% to about 40%, preferably from about 10% to about 30%, most preferably from about 15% to about 20%, of sodium citrate with from about 5% to about 30%, preferably from about 7% to 25%, most preferably from about 8% to about 20% sodium carbonate.

Water-Soluble Silicates

The present automatic dishwashing detergent compositions may further comprise water-soluble silicates. Water-soluble silicates herein are any silicates which are soluble to the extent that they do not adversely affect spotting/filming characteristics of the ADD composition.

Examples of silicates are sodium metasilicate and, more generally, the alkali metal silicates, particularly those having a $SiO_2$:$Na_2O$ ratio in the range 1.6:1 to 3.2:1; and layered silicates, such as the layered sodium silicates described in U.S. Pat. No. 4,664,839, issued May 12, 1987 to H. P. Rieck. NaSKS-6® is a crystalline layered silicate marketed by Hoechst (commonly abbreviated herein as "SKS-6"). Unlike zeolite builders, Na SKS-6 and other water-soluble silicates useful herein do not contain aluminum. NaSKS-6 is the δ-$Na_2SiO_5$ form of layered silicate and can be prepared by methods such as those described in German DE-A-3,417, 649 and DE-A-3,742,043. SKS-6 is a preferred layered silicate for use herein, but other such layered silicates, such as those having the general formula $NaMSi_xO_{2x+1}·yH_2O$ wherein M is sodium or hydrogen, x is a number from 1.9 to 4, preferably 2, and y is a number from 0 to 20, preferably 0 can be used. Various other layered silicates from Hoechst include NaSKS-5, NaSKS-7 and NaSKS-11, as the α-, β- and γ- forms. Other silicates may also be useful, such as for example magnesium silicate, which can serve as a crispening agent in granular formulations, as a stabilizing agent for oxygen bleaches, and as a component of suds control systems.

Silicates particularly useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Material Care Agents

The preferred ADD compositions may contain one or more material care agents which are effective as corrosion inhibitors and/or anti-tarnish aids. Such materials are preferred components of machine dishwashing compositions especially in certain European countries where the use of electroplated nickel silver and sterling silver is still comparatively common in domestic flatware, or when aluminum protection is a concern and the composition is low in silicate. Generally, such material care agents include metasilicate, silicate, bismuth salts, manganese salts, paraffin, triazoles, pyrazoles, thiols, mercaptans, aluminum fatty acid salts, and mixtures thereof.

When present, such protecting materials are preferably incorporated at low levels, e.g., from about 0.01% to about 5% of the ADD composition. Suitable corrosion inhibitors include paraffin oil, typically a predominantly branched aliphatic hydrocarbon having a number of carbon atoms in the range of from about 20 to about 50; preferred paraffin oil is selected from predominantly branched $C_{25-45}$ species with a ratio of cyclic to noncyclic hydrocarbons of about 32:68. A paraffin oil meeting those characteristics is sold by Wintershall, Salzbergen, Germany, under the trade name WINOG 70. Additionally, the addition of low levels of bismuth nitrate (i.e., $Bi(NO_3)_3$) is also preferred.

Other corrosion inhibitor compounds include benzotriazole and comparable compounds; mercaptans or thiols including thionaphtol and thioanthranol; and finely divided Aluminum fatty acid salts, such as aluminum tristearate. The formulator will recognize that such materials will generally be used judiciously and in limited quantities so as to avoid any tendency to produce spots or films on glassware or to compromise the bleaching action of the compositions. For this reason, mercaptan anti-tarnishes which are quite strongly bleach-reactive and common fatty carboxylic acids which precipitate with calcium in particular are preferably avoided.

Adjunct Materials

Detersive ingredients or adjuncts optionally included in the instant compositions can include one or more materials for assisting or enhancing cleaning performance, treatment of the substrate to be cleaned, or designed to improve the aesthetics of the compositions. Adjuncts which can also be included in compositions of the present invention, at their conventional art-established levels for use (generally, adjunct materials comprise, in total, from about 30% to about 99.9%, preferably from about 70% to about 95%, by weight of the compositions), include other active ingredients such as non-phosphate builders, chelants, enzymes, suds suppressors, dispersant polymers (e.g., from BASF Corp. or Rohm & Haas), color speckles, silvercare, anti-tarnish and/or anti-corrosion agents, dyes, fillers, germicides, alkalinity sources, hydrotropes, anti-oxidants, enzyme stabilizing agents, perfumes, solubilizing agents, carriers, processing aids, pigments, and pH control agents.

Depending on whether a greater or lesser degree of compactness is required, filler materials can also be present in the instant ADDs. These include sucrose, sucrose esters, sodium sulfate, potassium sulfate, etc., in amounts up to about 70%, preferably from 0% to about 40% of the ADD composition. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Hydrotrope materials such as sodium benzene sulfonate, sodium toluene sulfonate, sodium cumene sulfonate, etc., can be present, e.g., for better dispersing surfactant.

Bleach-stable perfumes (stable as to odor); and bleach-stable dyes such as those disclosed in U.S. Pat. No. 4,714,562, Roselle et al, issued Dec. 22, 1987 can also be added to the present compositions in appropriate amounts.

Since ADD compositions herein can contain water-sensitive ingredients or ingredients which can co-react when brought together in an aqueous environment, it is desirable to keep the free moisture content of the ADDs at a minimum, e.g., 7% or less, preferably 5% or less of the ADD; and to provide packaging which is substantially impermeable to water and carbon dioxide. Coating measures have been described herein to illustrate a way to protect the ingredients from each other and from air and moisture. Plastic bottles, including refillable or recyclable types, as well as conventional barrier cartons or boxes are another helpful means of assuring maximum shelf-storage stability. As noted, when ingredients are not highly compatible, it may further be desirable to coat at least one such ingredient with a low-foaming nonionic surfactant for protection. There are numerous waxy materials which can readily be used to form suitable coated particles of any such otherwise incompatible components; however, the formulator prefers those materials which do not have a marked tendency to deposit or form films on dishes including those of plastic construction.

The following nonlimiting examples further illustrate the ADD compositions of the present invention.

|  | Weight % | |
| --- | --- | --- |
| Ingredients: | A | B |
| Sodium Tripolyphosphate (STPP) | 28.0 | 30 |
| Sodium carbonate | 30.0 | 28.0 |
| Hydrated 2.0r silicate | 5 | 2 |
| nonionic surfactants | 1.0 | 2.0 |
| Protease[1] (4% active) | 0.43 | 0.75 |
| Amylase (1.6% active) | 0.46 | 0.46 |
| Perborate monohydrate (15.5% Active AvO)[2] | 14.5 | 14.5 |
| Water, sodium sulfate and misc. | Balance | Balance |

[1]"Protease D" according to the present invention comprising protease D core material, a sodium citrate dihydrate barrier layer and a HPMC over-layer.

[2]The AvO level of the above formula is 2.2%. The perborate is obtained from DeGussa Corp.

The ADD's of the above dishwashing detergent composition examples are used to wash milk-soiled glasses, by loading the soiled dishes in a domestic automatic dishwashing appliance and washing using either cold fill, 60° C. peak, or uniformly 45–50° C. wash cycles with a product concentration of the exemplary compositions of from about 1,000 to about 8,000 ppm, with excellent cleaning and spotting and filming results.

What is claimed is:

1. A detersive enzyme composite particle suitable for incorporation in a detergent composition comprising:
   (a) an enzyme containing core material;
   (b) a barrier layer coated on said enzyme containing core material, said barrier layer including nitrogen-based cation or a water-soluble salt of a metals selected from the group consisting of citrates, succinates and maleates, where said barrier layer is employed at levels 10% to about 30% by weight of the total weight of the enzyme composite particle a non-polymeric.

2. The composite particle as claimed in claim 1 wherein said enzyme containing core material comprises a protease enzyme.

3. The composite particle as claimed in claim 2 wherein said protease enzyme comprises a non-naturally-occurring carbonyl hydrolase variants having an amino acid sequence not found in nature, which is derived by replacement of a plurality of amino acid residues corresponding to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274 of a precursor carbonyl hydrolase with different amino acids, where the numbered position corresponds to naturally-occurring subtilisin from *Bacillus amyloliquefaciens*.

4. The composite particle as claimed in claim 3 wherein said protease enzyme is a non-naturally-occurring carbonyl hydrolase variants having an amino acid sequence not found in nature, which is derived by replacement of a plurality of amino acid residues corresponding to positions 76/103/104 of a precursor carbonyl hydrolase with different amino acids, where the numbered position corresponds to naturally-occurring subtilisin from *Bacillus amyloliquefaciens*.

5. The composite particle as claimed in claim 2 wherein said enzyme core material comprises a mixture of at least two different protease enzymes.

6. The composite particle as claimed in claim 5 wherein said mixture of at least two protease enzymes comprise at least one chymotrypsin-like protease enzyme and at least one trypsin-like protease enzyme.

7. The composite particle as claimed in claim 6 wherein said chymotrypsin-like protease enzyme is a non-naturally-occurring carbonyl hydrolase variants having an amino acid sequence not found in nature, which is derived by replacement of a plurality of amino acid residues corresponding to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274 of a precursor carbonyl hydrolase with different amino acids, where the numbered position corresponds to naturally-occurring Rubtilisin from Bacillus amyloliquefaciens and said trypsin-like protease enzyme is a microbial alcaline proteinase.

8. The composite particle as claimed in claim 1 wherein said composite particle further comprises an outer overlayer coated on said barrier layer.

9. The composite particle as claimed in claim 8 wherein said overlayer coated on said barrier layer is a water-soluble polymer.

10. The composite particle as claimed in claim 1 wherein said enzyme containing core material further includes a bleach catalyst material.

11. The composite particle as claimed in claim 8 wherein said composite particle further comprises a stabilizing additive admixed in any or all of said enzyme containing core material, said barrier layer and said overcoat.

12. The composite particle as claimed in claim 11 wherein said stabilizing additive is selected from the group consisting of alkaline salts, antioxidants, radical quenchers, reducing agents, chelants and mixtures thereof.

13. The composite particle as claimed in claim 12 wherein said stabilizing additive is an alkali metal sulfite, bisulfite or thiosulfate.

14. The composite particle as claimed in claim 1 wherein said water-soluble salt is sodium citrate dihydrate.

15. An automatic dishwashing composition comprising:
   (a) from about 0.1% to about 10% by weight of the composition of a composite detersive enzyme particle, said enzyme particle having an enzyme containing core material and a barrier layer coated on said enzyme containing core material, said barrier layer including a non-polymeric, water-soluble salt of a metal or nitrogen-based cation, wherein said water-soluble salt is selected from the group consisting citrates, succinates and maleates. and mixtures thereof, and,
   (b) from about 0.1% to about 99.9% by weight of the composition of adjunct automatic dishwashing detergent ingredients.

16. The composition as claimed in claim 15 wherein said adjunct detergent ingredients selected from the group consisting of a source of peroxygen bleach, bleach catalysts, bleach activators, low-foaming nonionic surfactants, builders, pH-adjusting components, and mixtures thereof.

17. The composition as claimed in claim 15 wherein the enzyme in said enzyme containing core material is a protease enzyme being a non-naturally-occurring carbonyl hydrolase variants having an amino acid sequence not found in nature, which is derived by replacement of a plurality of amino acid residues corresponding to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274 of a precursor carbonyl hydrolas with different amino acids, where the numbered position corresponds to naturally-occurring subtilisin from *Bacillus amyloliquefaciens*.

18. The composition as claimed in claim 15 wherein said protease enzyme is a non-naturally-occurring carbonyl hydrolase variants having an amino acid sequence not found in nature, which is derived by replacement of a plurality of amino acid residues corresponding to positions 76/103/104 of a precursor carbonyl hydrolase with different amino acids, where the numbered position corresponds to naturally-occurring subtilisin from *Bacillus amyloliquefaciens*.

19. The composition as claimed in claim 18 further comprising an additional protease enzyme admixed in said enzyme containing core material, said additional protease enzyme being a microbial alcaline proteinase.

20. The composition as claimed in claim 15 wherein said composite particle further comprises an outer overlayer coated on said barrier layer.

21. The composition as claimed in claim 15 wherein said enzyme containing core material furthers includes a bleach catalyst material.

22. The composition as claimed in claim 20 wherein said composite particle further comprises a stabilizing additive admixed in any or all of said enzyme containing core material, said barrier layer and said overcoat.

23. The composition as claimed in claim 22 wherein said stabilizing additive is selected from the group consisting of alkaline salts, antioxidants, radical quenchers, reducing agents, chelants and mixtures thereof.

24. The composition as claimed in claim 23 wherein said stabilizing additive is an alkali metal sulfite, bisulfite or thiosulfate.

25. The composite particle as claimed in claim 15 wherein said water-soluble salt is sodium citrate dihydrate.

* * * * *